United States Patent [19]

Boss

[11] 4,124,027
[45] Nov. 7, 1978

[54] CONTROLLED RELEASE SUTURES
[75] Inventor: Arthur E. Boss, Mountainside, N.J.
[73] Assignee: Ethicon, Inc., Somerville, N.J.
[21] Appl. No.: 774,305
[22] Filed: Mar. 4, 1977
[51] Int. Cl.² ............................................. A61B 17/06
[52] U.S. Cl. ......................................... 128/339; 163/1
[58] Field of Search ............................. 128/335.5, 339; 223/102; 163/1, 5

[56] References Cited
U.S. PATENT DOCUMENTS

| 2,728,343 | 12/1955 | Everett | 128/339 |
| 2,910,983 | 11/1959 | Everett | 128/339 |
| 3,924,630 | 12/1975 | Walldorf | 128/339 |
| 4,054,144 | 10/1977 | Hoffman et al. | 128/339 |

Primary Examiner—Dalton L. Truluck
Attorney, Agent, or Firm—Wayne R. Eberhardt

[57] ABSTRACT

A controlled release needle-suture combination wherein a fluid swellable suture is attached to a surgical needle having an oversized blind axial opening by inserting the suture into the full depth of the opening and swaging the needle over the outermost portion of the opening so that the end of the suture at the innermost portion of the opening remains uncompressed. Such needle-suture combinations are characterized by having relatively uniform and consistent needle pull-off values regardless of changes in the fluid content of the suture.

23 Claims, 6 Drawing Figures

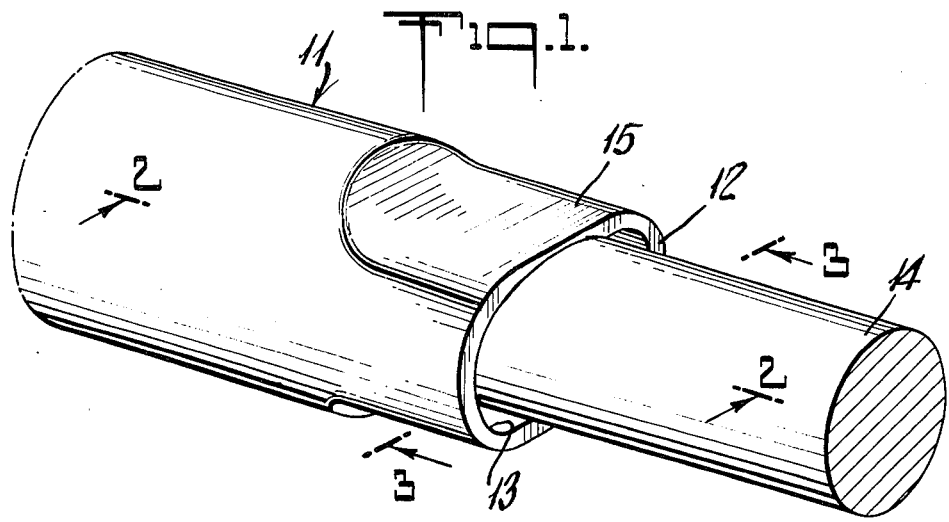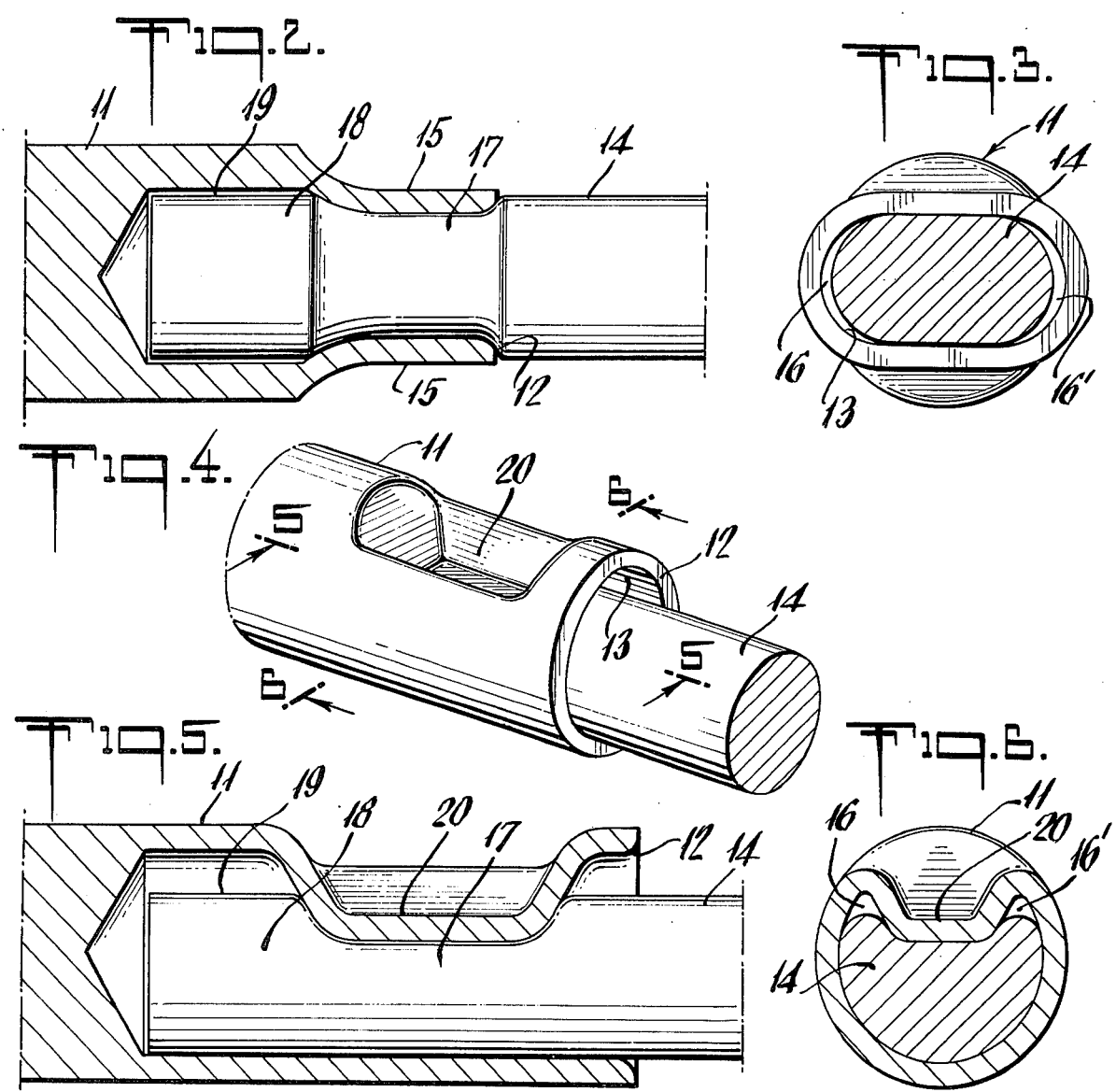

CONTROLLED RELEASE SUTURES

BACKGROUND OF THE INVENTION

1. Field of the Invention

This invention relates to needle-suture combinations and more particularly to needle-suture combinations comprising fluid swellable sutures and surgical needles attached to the suture by swaging so that the needle is removable by a force of from about 3 to 26 ounces.

2. Description of Prior Art

The concept of a needle-suture combination having a removable swaged needle was first described in U.S. Pat. No. 3,890,975. Such a needle-suture combination is more convenient for the surgeon since after completing the suturing procedure, the needle can be removed from the suture by a quick tug, whereas conventional sutures require the needle to be cut from the suture.

Subsequent to U.S. Pat. No. 3,890,975, several techniques have been proposed for providing needle-suture combinations of different types and compositions with removable needles. These are described, for example, in U.S. Pat. Nos. 3,875,946; 3,926,164; 3,943,933; 3,949,756; 3,963,031 and 3,981,307.

The methods described in the above patents provide needle-suture combinations having suture pull-out values within the desirable range at the time of manufacture. With suture materials that are relatively dimensionally stable under normal storage conditions, the sutures will retain a pull-out value within the desirable range until the time of use in the operating room. With certain fluid swellable sutures, however, particularly collagenous sutures including both natural collagen strands called "gut" and extruded collagen, there is considerable variation in the volume of the suture with varying moisture content and therefore, a needle-suture combination of these materials may have substantially different suture pull-out values at different moisture contents.

The problem of variable suture pull-out values is particularly acute with respect to needle-suture combinations utilizing collagenous sutures which are wet packed and stored in hermetically sealed envelopes containing a fluid such as an alcohol-water solution to maintain the suture in a pliable state. If the needle-suture combination is manufactured to have a suitable pull-out value when the collagenous material is in a dry state, it may have too high a pull-out value after suture has absorbed water from the aqueous alcohol solution and expanded within the swaged junction of the needle. Conversely, if the needle-suture combination is manufactured to have a suitable pull-out value when the collagenous material has a high moisture content, it may have too low a pull-out value or may not hold together at all if it is allowed to dry out before use.

The difficulty associated with the preparation of controlled release fluid swellable sutures was recognized in U.S. Pat. No. 3,924,630 where it was suggested to dimension the needle opening to provide in the swaged portion of the needle a cross-sectional area equal to from about 150 to about 250% of the cross-sectional area of the suture when the suture was in nonswollen state. The excess volume in the needle opening was discovered to allow for expansion in volume of the suture due to an increase in moisture content without a major increase in suture pull-out value. It has now been discovered, however, that suture pull-out values may decrease to less than preferred levels when a moist suture is allowed to dry and the volume of the suture decreases. The present invention is an improvement over the method and product of the '630 patent which reduces the variability of suture pull-out values resulting from variations in the moisture content of fluid swellable sutures.

It is accordingly an object of the present invention to provide an improved method for attaching needles to fluid swellable sutures whereby the suture pull-out value does not vary beyond acceptable limits with changes in suture fluid content. It is a further object of the present invention to provide a method for attaching needles to catgut sutures so that the suture pull-out value is within the range of 3 to 26 ounces regardless of suture moisture content. It is a yet further object of this invention to provide improved needle-suture combinations comprising fluid swellable sutures with a drilled needle attached thereto by swaging and characterized in that the needle may be removed by a force of 3 to 26 ounces regardless of the extent to which the suture is swollen by presence of moisture. These and other objects of this invention will be apparent from the ensuing description and claims.

SUMMARY

In accordance with the present invention, a needle-suture combination comprising a fluid swellable suture swaged to a surgical needle and having a suture pull-out value of from 3 to 26 ounces is obtained by providing a suture receiving axial opening in the needle having a diameter of from 1.2 to 2.0 times the diameter of the suture to be inserted therein, and attaching the needle to the suture by inserting the suture into the needle opening and swaging the needle within the boundaries of an area extending between the blunt end of the needle and a point intermediate the blunt end and the blind end of the axial opening therein so that the tip of the suture remains uncompressed and a suture pull-out value from about 3 to 26 ounces is obtained.

In accordance with the present invention, the suture is restrained within the axial opening of the needle by two factors. First, there is direct compression upon the suture by the needle barrel in the area of the swage. This force corresponds to that found in conventional swaged needle attachment. The second restraining factor is the restriction upon the uncompressed tip of the suture imposed by the swaged portion of the needle barrel through which the tip of the suture must be drawn to remove the suture from the needle.

The two suture restraining factors cooperate in the unique manner to maintain the suture pull-out value within desirable limits regardless of the moisture content or swollen state of the suture. As the moisture content of the suture increases, the suture swells in cross-sectional area and the compressive forces on the suture within the swaged portion of the needle barrel increase and tend to increase suture pull-out values. Simultaneously, however, as the moisture content of the suture increases, the suture softens and becomes more easily deformable. This effect tends to decrease compressive forces on the suture within the swaged portion of the needle to reduce suture pull-out values. A greater effect, however, is in the increased ease with which the unswaged tip of the suture may be deformed and withdrawn through the swaged portion of the needle barrel which also tends to decrease suture pull-out value.

Conversely, when suture moisture content is decreased, there is an opposite effect on the suture restraining factors which are also offsetting in their effect on suture pull-out values. As suture moisture content decreases, the diameter of the suture contracts and the compressive forces within the swaged area of the needle are reduced tending to reduce suture pull-out value. Simultaneously, however, the suture becomes harder and less readily deformed with a consequent increase in the force required to withdraw the uncompressed portion of the suture through the swaged section of the needle barrel. Thus, the two suture restraining forces react in opposite ways to changes in suture moisture content and tend to be offsetting in their effect on suture pull-out values.

BRIEF DESCRIPTION OF DRAWINGS

FIG. 1 is an enlarged fragmentary perspective view of a needle-suture combination of the present invention illustrating a needle attached by flat swaging.

FIG. 2 is a cross-sectional view at plane 2—2 of FIG. 1 showing the axial opening in the needle and the suture positioned therein.

FIG. 3 is a further enlarged cross-sectional view at plane 3—3 of FIG. 1 showing the suture within the swaged portion of the needle barrel.

FIG. 4 is an enlarged fragmentary perspective view of a needle-suture combination illustrating a needle attached by stake swaging.

FIG. 5 is a cross-sectional view at plane 5—5 of FIG. 4 showing the axial opening in the needle and the suture positioned therein.

FIG. 6 is a further enlarged cross-sectional view at plane 6—6 of FIG. 4 showing the suture within the swaged portion of the needle barrel.

DETAILED DESCRIPTION OF INVENTION

With reference to FIG. 1, needle 11 has a blunt end 12 containing axial opening 13 into which one end of suture 14 is inserted. Flat swaging produces swaged faces 15 on the needle barrel and causes the deformation of that portion of the suture 17 within the swaged area of the needle opening as shown in FIG. 2.

FIG. 2 additionally shows that axial opening 13 extends into the needle beyond the swaged area to provide a substantially undeformed portion of opening 19 wherein there is contained a substantially uncompressed portion 18 of the suture.

FIG. 3 illustrates spaces 16 on either side of suture 14 within the swaged area of hole 13 which result from utilizing a needle having a drilled hole with a diameter of from about 1.2 to 2.0 times the diameter of the suture to be swaged therein.

FIGS. 4–6 illustrate a needle-suture combination wherein the needle is attached by stake swage 20 in views corresponding to FIGS. 1–3, respectively, for a needle-suture combination attached by flat swaging.

With further reference to FIG. 2, there is shown the two portions of the suture identified as 17 and 18 which serve to restrain the suture within the needle. Upon absorption of moisture, the suture expands in diameter so that the compressive forces on portion 17 are increased. Uncompressed portion 18 of the suture, meanwhile, is free to expand in section 19 of axial opening 13. The expansion of the suture tends to increase the restraining forces on portion 17 and consequently increases the suture pull-out value. There is, however, a simultaneous softening of the suture which allows portion 19 to be more easily deformed and withdrawn through the narrow swaged portion of the needle with a consequent decrease in suture pull-out value which tends to offset the increase resulting from additional compressive forces on portion 17 of the suture.

When the moisture content of the suture is reduced, an opposite effect takes place. The suture contracts in diameter and hardens so that the compressive forces on section 17 are reduced, but the force required to withdraw the hardened, undeformed section 19 through the narrow swaged portion of the needle is increased. The net result of these offsetting effects is that the suture pull-out value remains relatively constant throughout the moistening and drying cycles.

The needle is preferably swaged within the boundaries of an area extending from the blunt end of the needle to about 30 to 70 percent of the length of the axial opening. In the case of flat swaging, the swaged portion may include this entire area. In the case of stake swaging, the swage will generally cover only a small portion of the designated area as illustrated in FIGS. 4 and 5. The degree of compression in the swaged area required to provide the desired suture pull-out value will vary according to the area and type of swage. Typically, flat swaging over a larger area will require less compression of the suture to obtain a given pull-out value than a flat swage over a smaller area, or a stake swage. The degree of compression is accordingly controlled to provide a suture pull-out value within the range of from about 3 to 26 ounces when first attaching the suture to the needle.

The ratio of the length of the uncompressed tip portion of the suture to the diameter of the suture is preferably at least about 1:1, and most preferably from about 1.5:1 to 5:1. When the ratio is less than about 1:1, the amount of uncompressed suture is so small that the effect of this element on suture pull-out value as above described becomes insignificant. Conversely, when the ratio is greater than about 5:1, the effect of this element on suture pull-out value becomes dominant.

The needle-suture combinations of the present invention are most conveniently prepared by attaching drilled needles to dry sutures by swaging to provide the desired suture pull-out value. The thus assembled needle-suture combinations may be soaked or packaged in an aqueous solution to soften and pliabilize the suture with the assurance that the suture pull-out value will not deviate beyond acceptable levels as a result of suture expansion due to moisture absorption.

The method and product of the present invention is further illustrated by the following examples.

EXAMPLES

A series of natural gut sutures ranging in size from 3-0 to 1 (diameters 0.011 to 0.020 inches) were inserted in a dry state into drilled needles having an oversized suture receiving axial opening in the needle barrel. The needles were flat swaged over about 50% of the total depth of the drilled hole so that the resulting suture pull-out value was in the range of 3-26 ounces.

In a typical evaluation of suture pull-out values, two hundred sutures of a given type are prepared under identical conditions. Fifty samples selected at random are pull tested to obtain initial suture pull-out values for the sample. The remaining 150 sutures are placed in an aqueous solution of 90% isopropyl alcohol for a period of several days to reach an equilibrium moisture content. Fifty samples selected at random are pull tested wet to determine the suture pull-out value for the moistened sutures. The remaining 100 sutures are dried at room temperature and humidity for a period of about 3 hours. Fifty samples selected at random are pull tested after drying to determine the suture pull-out value after one dry-wet-dry cycle. The remaining sutures are again soaked in deionized water for 2 to 3 hours and the pull tested wet to determine suture pull-out values after a complete dry-wet-dry-wet cycle.

In Examples I–V given in Table I, suture sample sizes ranged from 200 to 300 sutures. In Examples I and II, control samples were prepared by flat swaging the needles over substantially the full length of the axial opening. The control sutures of Example I correspond substantially to those prepared according to the method of U.S. Pat. No. 3,924,630. The ratio of needle hole to suture diameter in the control sutures of Example II was less than recommended in the '630 patent.

the generally small deviation from initial suture pull-out values as a result of changes in moisture content. Of these Examples, only the "rewet" data for Example IV was considered to be beyond acceptable limits. Even better results and less variability would be expected in needle-suture combinations manufactured under production rather than laboratory conditions.

The needles of the needle-suture combinations of the present invention are preferably drilled needles having relatively smooth and uniform internal surfaces. Closed channel needles can be used although the variability in internal hole diameter will result in greater variability of suture pull-out values. If closed channels are to be used, it is preferred that the channel be closed about a mandrel or that the closed channel be reamed to obtain a smooth uniform opening.

The needles may be attached to the suture by flat, stake, square or other swage design. The suture may be

TABLE Ia

| Example | | I | | II |
|---|---|---|---|---|
| Nominal suture size | | 3–0 | | 0 |
| Suture diameter, in. (mm) | | 0.011(.279) | | 0.017(.432) |
| Needle hole diameter, in. (mm) | | 0.016(.406) | | 0.020(.508) |
| Needle hole/Suture diameter | | 1.45 | | 1.18 |
| Depth of needle hole, in. (mm) | | 0.067(1.70) | | 0.070(1.78) |
| Length of swage, in. (mm) | | Full 0.035(.889) | | Full 0.039(.889) |
| Swage length/Hole depth, % | | 100 52 | | 100 50 |
| Uncompressed length of suture, in. (mm) | | 0 0.032(.813) | | 0 0.035(.889) |
| Uncompressed length/Suture diameter | | 0 2.9:1 | | 0 2.1:1 |
| Suture pull-out, oz. (gm) | | | | |
| Initial | - Mean | 15.3(434) | 13.2(374) | 16.0(454) | 10.4(295) |
| | - Std. dev. | 3.6(102) | 3.5( 99) | 3.0( 85) | 3.2( 91) |
| Wet | - Mean | 13.0(369) | 8.0(227) | 17.4(493) | 6.0(170) |
| | - Std. dev. | 2.8( 79) | 1.3( 39) | 5.0(142) | 1.7( 48) |
| Redried | - Mean | 12.6(357) | 16.6(471) | 5.8(164) | 14.2(403) |
| | - Std. dev. | 3.8(108) | 3.2( 91) | 4.5(128) | 2.5( 71) |
| Rewet | - Mean | 9.1(258) | 17.3(490) | 26.9(763) | 17.7(502) |
| | - Std. dev. | 3.8(108) | 2.4( 68) | 4.3(122) | 3.0( 85) |

TABLE Ib

| Example | | III | | IV | | V | |
|---|---|---|---|---|---|---|---|
| Nominal suture size | | 00 | | 0 | | 1 | |
| Suture diameter, in. (mm) | | .0138 | ( .35) | .0168 | ( .43) | .0192 | ( .49) |
| Needle hole diameter, in. (mm) | | .0175 | ( .44) | .0217 | ( .55) | .0248 | ( .63) |
| Needle hole/Suture diameter | | 1.27 | | 1.29 | | 1.29 | |
| Depth of needle hole, in. (mm) | | .067 | (1.7) | .070 | (1.8) | .070 | (1.78) |
| Length of swage, in. (mm) | | .035 | ( .90) | .035 | ( .90) | .035 | ( .90) |
| Swage length/Hole depth, % | | 52 | | 50 | | 50 | |
| Uncompressed length of suture, in. (mm) | | .032 | ( .81) | .035 | ( .90) | .035 | ( .90) |
| Uncompressed length/Suture diameter | | 2.3 | | 2.1 | | 1.8 | |
| Suture pull-out, oz. (gm) | | | | | | | |
| Initial | - Mean | 14.3 | (405) | 12.2 | (346) | 13.7 | (388) |
| | - Std. dev. | 3.5 | ( 99) | 3.2 | ( 91) | 4.0 | (113) |
| Wet | - Mean | 12.4 | (352) | 11.3 | (320) | 11.1 | (315) |
| | - Std. dev. | 2.8 | ( 79) | 2.7 | ( 77) | 3.6 | (102) |
| | - % Initial | 87 | | 93 | | 81 | |
| Redried | - Mean | 13.7 | (388) | 16.8 | (476) | 16.2 | (459) |
| | - Std. dev. | 3.0 | ( 85) | 4.8 | (136) | 5.9 | (167) |
| | - % Initial | 96 | | 137 | | 118 | |
| Rewet | - Mean | 11.7 | (332) | 26.3 | (746) | 10.5 | (298) |
| | - Std. dev. | 4.2 | (119) | 5.0 | (142) | 3.3 | ( 94) |
| | - % Initial | 82 | | 216 | | 77 | |

The data in Table I illustrate that the present invention provides an improved and desirable method for preparing controlled release needle-suture combinations with fluid swellable sutures. Example I illustrates that in each instance, sutures prepared in accordance with the present invention had more uniformity (lower standard deviations) in suture pull-out values within groups of test sutures than comparable sutures attached by full swaging. Similar results are seen in a comparison of the control and test samples in Example II.

Examples III–V illustrate the low degree of variability within sample groups (low standard deviation) and plain or chrome-tanned catgut or extruded collagen and of any size. The sutures are preferably prepared with uniform diameters since variations in suture diameter between batches of sutures of the same nominal size will result in variability of suture pull-out values unless swaging conditions are adjusted for each batch.

The above and other variations of the present invention will be apparent to those skilled in the art and such apparent variations are included within the scope of the present invention.

I claim:

1. In a needle-suture combination having a removable needle and comprising a needle having a pointed end and a blunt end and having a blind axial opening extending into said needle from said blunt end, and a fluid swellable suture inserted into said axial opening of said needle and secured therein by swaging, the improvement comprising dimensioning the diameter of the axial opening of the needle to about 1.2 to 2.0 times the diameter of the unswollen suture inserted therein, and swaging the needle and suture within the boundaries of an area extending from the blunt end of the needle to a point between said blunt end and the blind end of said axial opening so that a segment of the tip of the suture within said axial opening and extending from the blind end of the axial opening to the swaged portion of the needle remains substantially uncompressed, said construction of swaged needle and suture providing means of reducing the variability in the force required to remove the needle as a result of changes in suture fluid content.

2. A needle-suture combination of claim 1 wherein the area including the swaged portion of the needle extends from the blunt end of the needle to about 30-70% of the length of the axial opening.

3. A needle-suture combination of claim 1 wherein the length of the uncompressed segment of the suture is at least equal to the diameter of the suture.

4. A needle-suture combination of claim 3 wherein the length of the uncompressed segment of the suture is from 1.5 to 5 times the diameter of the suture.

5. A needle-suture combination of claim 1 wherein said suture comprises a water swellable collagen selected from the group consisting of natural collagen and extruded collagen.

6. A needle-suture combination of claim 5 wherein said combinations are packaged in an aqueous alcohol solution.

7. A needle-suture combination of claim 6 wherein said solution comprises about 90% by volume of isopropyl alcohol and about 10% by volume of water.

8. A needle-suture combination of claim 5 wherein the diameter of the dry suture is from about 0.15 to about 0.6 millimeters.

9. A needle-suture combination of claim 8 where in the length of the uncompressed segment of the suture is at least equal to the diameter of the suture.

10. A needle-suture combination of claim 8 where in the length of the uncompressed segment of the suture is from about 1.5 to 5 times the diameter of the suture.

11. A needle-suture combination of claim 1 wherein the force required to remove the needle is from about 3 ounces to about 26 ounces.

12. A needle-suture combination of claim 5 wherein the force required to remove the needle is from about 3 ounces to about 26 ounces.

13. A needle-suture combination of claim 1 wherein said suture is secured in said needle by flat swaging.

14. A needle-suture combination of claim 1 wherein said suture is secured in said needle by stake swaging.

15. The needle-suture combination of claim 1 wherein said axial opening is a drilled hole.

16. A needle-suture combination of claim 1 wherein the needle is swaged over a central segment of the axial opening and end segments at each end of said axial opening and the suture contained therein remain substantially uncompressed.

17. In a method for making a needle-suture combination having a removable needle wherein a needle having a sharp end and a blunt end is attached at its blunt end to a suture comprising a fluid swellable material by the insertion of one tip of said suture into a blind axial opening in said blunt end followed by a swaging of said blunt end and the distortion of said opening to bring at least a portion of the inner surface of said opening into tight engagement with said suture tip, the improvement comprising dimensioning the diameter of the axial opening of the needle to about 1.2 to 2.0 times the diameter of the unswollen suture inserted therein, and swaging the needle and suture within the boundaries of an area extending from the blunt end of the needle to a point between said blunt end and the blind end of said axial opening so that a segment of the tip of the suture within said axial opening and extending from the blind end of the axial opening to the swaged portion of the needle remains substantially uncompressed whereby the variability in the force required to remove the needle as a result of changes in suture fluid content is substantially reduced.

18. A method of claim 17 wherein said swaging is flat swaging.

19. A method of claim 17 wherein said swaging is stake swaging.

20. A method of claim 17 wherein said suture comprises a collagenous material.

21. A method of claim 17 wherein the length of the uncompressed segment of the suture is at least equal to the diameter of the suture.

22. A method of claim 17 wherein the length of the uncompressed segment of the suture is from about 1.5 to 5 times the diameter of the suture.

23. A method of claim 17 wherein the needle is swaged over a central segment of the axial opening and end segments at each end of said axial opening and the suture contained therein remains substantially uncompressed.

* * * * *